(12) United States Patent
Bayyana et al.

(10) Patent No.: US 11,315,679 B2
(45) Date of Patent: Apr. 26, 2022

(54) SYSTEMS AND METHODS FOR PREDICTION BASED CARE RECOMMENDATIONS

(71) Applicant: Cigna Intellectual Property, Inc., Wilmington, DE (US)

(72) Inventors: Tayaru Bayyana, Highlands Ranch, CO (US); Ankur Kaneria, Cedar Park, TX (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 0 days.

(21) Appl. No.: 17/318,648

(22) Filed: May 12, 2021

(65) Prior Publication Data

US 2021/0265051 A1   Aug. 26, 2021

(51) Int. Cl.
*G16H 40/20* (2018.01)
*G16H 50/20* (2018.01)
(Continued)

(52) U.S. Cl.
CPC .......... *G16H 40/20* (2018.01); *G06F 16/254* (2019.01); *G06N 20/00* (2019.01); *G06Q 40/08* (2013.01);
(Continued)

(58) Field of Classification Search
CPC ........ G16H 40/20; G16H 10/60; G16H 50/70; G16H 50/20; G16H 70/20; G16H 50/80; G06N 20/00; G06F 16/254; G06Q 40/08
(Continued)

(56) References Cited

U.S. PATENT DOCUMENTS 10,831,863 B2   11/2020   De La Torre
10,885,150 B2   1/2021    De La Torre
(Continued)

OTHER PUBLICATIONS

"Preventing unnecessary emergency room visits to reduce health care costs" available at https://fractal.ai/wp-content/uploads/2018/06/Preventing-unnecessary-emergency-room-visits-to-reduce-health-care-costs.pdf (Jun. 2018).*
(Continued)

*Primary Examiner* — Jason S Tiedeman
(74) *Attorney, Agent, or Firm* — Schwegman Lundberg & Woessner

(57) ABSTRACT

A method for providing prediction based healthcare recommendations is performed by a healthcare prediction server. The method includes receiving an emergency room services request from a patient. The method also includes receiving a first portion of the plurality of historical claims data. The first portion includes associated historical outcome data. The method further includes applying a geospatial prevalence engine to the first portion of the plurality of historical claims data and the requestor location to identify at least one locally prevalent disease. The method additionally includes applying a claims processing engine to the first portion of the plurality of historical claims data and the requestor identifier to determine whether the patient is associated with at least one prior avoidable emergency room claim. The method includes predicting that the emergency room services request is associated with an avoidable visit. The method further includes transmitting an alternative services request.

20 Claims, 11 Drawing Sheets

(51) Int. Cl.
  *G16H 10/60* (2018.01)
  *G16H 50/80* (2018.01)
  *G06N 20/00* (2019.01)
  *G16H 70/20* (2018.01)
  *G16H 50/70* (2018.01)
  *G06F 16/25* (2019.01)
  *G06Q 40/08* (2012.01)

(52) U.S. Cl.
  CPC ............ *G16H 10/60* (2018.01); *G16H 50/20* (2018.01); *G16H 50/70* (2018.01); *G16H 50/80* (2018.01); *G16H 70/20* (2018.01)

(58) Field of Classification Search
  USPC .......................................................... 705/2, 3
  See application file for complete search history.

(56) References Cited

U.S. PATENT DOCUMENTS

| | | | |
|---|---|---|---|
| 2006/0106796 | A1 | 5/2006 | Venkataraman |
| 2009/0222539 | A1* | 9/2009 | Lewis ................... G16H 10/60 709/221 |
| 2010/0125186 | A1* | 5/2010 | Abuachi .............. A61B 5/0002 600/301 |
| 2013/0144650 | A1* | 6/2013 | Thesman ............... G16H 20/00 705/2 |
| 2014/0108034 | A1 | 4/2014 | Akbay |
| 2015/0019235 | A1 | 1/2015 | Roychowdhury |
| 2015/0039343 | A1* | 2/2015 | Cline .................... G16H 50/30 705/3 |
| 2015/0100343 | A1* | 4/2015 | Siedlecki ............... G16H 20/10 705/2 |
| 2015/0248532 | A1 | 9/2015 | Rajasenan |
| 2015/0254406 | A1 | 9/2015 | Rajasenan |
| 2017/0091406 | A1* | 3/2017 | Nguyen ................. G16H 50/70 |
| 2017/0161433 | A1* | 6/2017 | Perretta ................. G16H 30/20 |
| 2017/0372028 | A1* | 12/2017 | Zhou .................... G16H 40/20 |
| 2019/0088373 | A1 | 3/2019 | Sarmentero |
| 2019/0180868 | A1* | 6/2019 | Makram ............ G06Q 10/0631 |
| 2019/0214117 | A1 | 7/2019 | Lateef |
| 2019/0348180 | A1* | 11/2019 | Sharifi Sedeh ........ G16H 50/70 |
| 2019/0355082 | A1 | 11/2019 | Mcmillan |
| 2020/0105392 | A1* | 4/2020 | Karkazis ................ G16H 20/10 |
| 2021/0056419 | A1* | 2/2021 | Carr ...................... G06N 3/084 |
| 2021/0158909 | A1* | 5/2021 | Ng ......................... G16H 50/20 |
| 2021/0202103 | A1* | 7/2021 | Bostic .................... G16H 50/30 |

OTHER PUBLICATIONS

Fractal Analytics, Inc.; Healthcare Redirecting avoidable Emergency Room visits saves $10M with better health outcomes; www.fractalanalytics.com; Apr. 18, 2016.

* cited by examiner

SYSTEMS AND METHODS FOR PREDICTION BASED CARE RECOMMENDATIONS

FIELD

The field generally relates to systems in healthcare settings for identifying patients predicted to benefit from redirection in health care services from emergency room services to other services.

BACKGROUND

Patients experiencing medical problems frequently seek healthcare services from emergency rooms. However, in many cases, emergency room services are not the preferred services for those patients. For example, emergency room services may be more expensive to the patient and the provider. Further, patients often wait longer for services at an emergency room than they would need to wait if they sought services from urgent care or other service models. Significantly, patients with the same conditions often have worse outcomes when services are delivered at an emergency room than when they are delivered elsewhere.

However, in many cases, patients elect to use emergency room services without considering alternative options and thereby experience higher costs, longer waits, and worse outcomes. In some studies, patients who have elected to use emergency room services once have a high propensity to seek emergency room services again even when it is not warranted. Such patients may be eight times more likely to seek emergency services when it is not needed than a person who has not previously sought emergency room services. In other studies, analysts have determined that nearly one third of all emergency room visits by patients were unnecessary and that such patients would have benefitted from provision of services elsewhere. The cost savings are also significant. If a patient were able to avoid an unnecessary emergency room visit and seek services elsewhere, they may save thousands of dollars per visit. Nationally, patients may save millions of dollars by seeking services from alternative service models such as urgent care. However, because of a lack of information about how to evaluate alternative services, many patients default to emergency services.

BRIEF SUMMARY

In one aspect, a healthcare prediction system for providing prediction based healthcare recommendations is provided. The healthcare prediction system includes a first data warehouse system including a warehouse processor and a warehouse memory. The first data warehouse system further includes a plurality of historical claims data. The healthcare prediction system also includes a healthcare prediction server in communication with the first data warehouse system. The healthcare prediction server also includes a processor and a memory. The processor is configured to receive an emergency room services request from a patient. The emergency room services request includes a requestor location, a requestor identifier, and requestor symptoms. The processor is also configured to receive a first portion of the plurality of historical claims data from the data warehouse system. The first portion includes associated historical outcome data. The processor is further configured to apply a geospatial prevalence engine to the first portion of the plurality of historical claims data and the requestor location to identify at least one locally prevalent disease having associated locally prevalent disease symptoms. The processor is also configured to apply a claims processing engine to the first portion of the plurality of historical claims data and the requestor identifier to determine whether the patient is associated with at least one prior avoidable emergency room claim. Upon determining at least one of a) that the patient is associated with at least one prior avoidable emergency room claim and b) that the requestor symptoms match the locally prevalent disease symptom, the processor is further configured to predict that the emergency room services request is associated with an avoidable visit. The processor is also configured to transmit an alternative services request defined based on the requestor location, the requestor identifier, and the at least one symptom.

In another aspect, a method for providing prediction based healthcare recommendations is provided. The method is performed by a healthcare prediction server in communication with a first data warehouse system. The healthcare prediction server includes a processor and a memory. The first data warehouse system includes a warehouse processor and a warehouse memory. The first data warehouse system further includes a plurality of historical claims data. The method includes receiving an emergency room services request from a patient. The emergency room services request includes a requestor location, a requestor identifier, and requestor symptoms. The method also includes receiving a first portion of the plurality of historical claims data from the data warehouse system. The first portion includes associated historical outcome data. The method further includes applying a geospatial prevalence engine to the first portion of the plurality of historical claims data and the requestor location to identify at least one locally prevalent disease having associated locally prevalent disease symptoms. The method additionally includes applying a claims processing engine to the first portion of the plurality of historical claims data and the requestor identifier to determine whether the patient is associated with at least one prior avoidable emergency room claim. Upon determining at least one of a) that the patient is associated with at least one prior avoidable emergency room claim and b) that the requestor symptoms match the locally prevalent disease symptom, the method includes predicting that the emergency room services request is associated with an avoidable visit. The method further includes transmitting an alternative services request defined based on the requestor location, the requestor identifier, and the at least one symptom.

In yet another aspect, a healthcare prediction server for providing prediction based healthcare recommendations is provided. The healthcare prediction server is in communication with a first data warehouse system. The healthcare prediction server includes a processor and a memory. The first data warehouse system includes a warehouse processor and a warehouse memory. The first data warehouse system further includes a plurality of historical claims data. The processor is configured to receive an emergency room services request from a patient. The emergency room services request includes a requestor location, a requestor identifier, and requestor symptoms. The processor is also configured to receive a first portion of the plurality of historical claims data from the data warehouse system. The first portion includes associated historical outcome data. The processor is further configured to apply a geospatial prevalence engine to the first portion of the plurality of historical claims data and the requestor location to identify at least one locally prevalent disease having associated locally prevalent disease symptoms. The processor is also configured to apply a claims processing engine to the first portion of the plurality of historical claims data and the requestor identifier to determine whether the patient is associated with at least one prior avoidable emergency room claim. Upon determining at least one of a) that the patient is associated with at least one prior avoidable emergency room claim and b) that the requestor symptoms match the locally prevalent disease symptom, the processor is further configured to predict that the emergency room services request is associated with an avoidable visit. The processor is also configured to transmit an alternative services request defined based on the requestor location, the requestor identifier, and the at least one symptom.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

In the drawings, reference numbers may be reused to identify similar and/or identical elements.

DETAILED DESCRIPTION

Figure 1:
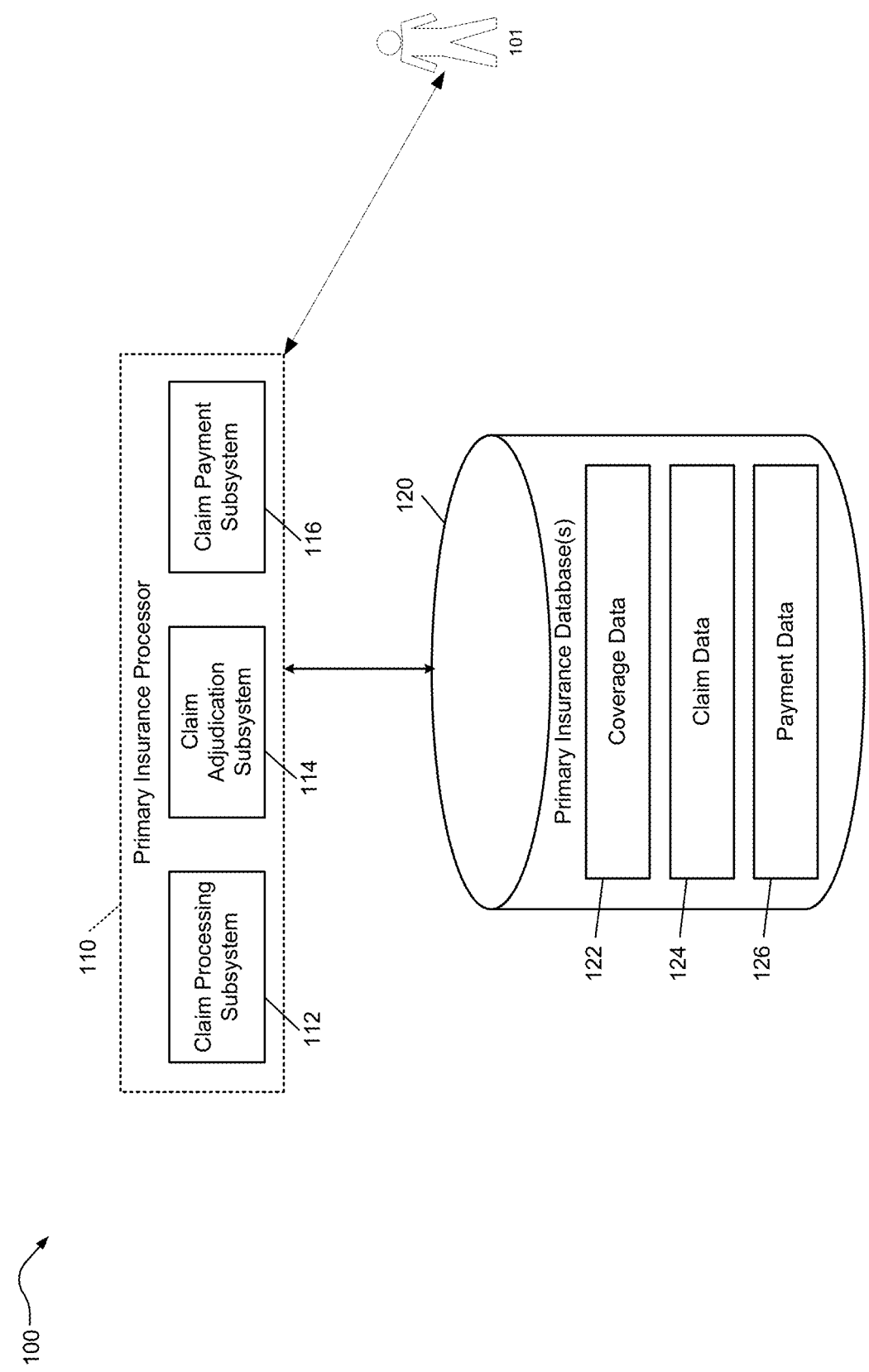
FIG. 1 is a functional block diagram of an example insurance claim processing system.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

To improve medical care systems and methods, systems and methods for identifying patients who should seek alternatives to emergency room services are desirable. However, the complexity of analysis of healthcare provision and the constantly changing nature of healthcare makes it difficult or impossible to determine static rules or methods for identifying such patients. Rather, any such systems or methods must incorporate changing conditions and variations in patients and patient demographics. Thus, to address the problems described herein, a technical solution is desired that is dynamic and incorporates machine learning.

In view of the technological challenges, systems and methods are desired for identifying patients predicted to benefit from redirection in health care services from emergency room services to other services.

As described herein, patients experiencing medical problems frequently seek healthcare services from emergency rooms. However, in many cases, emergency room services are not the preferred services for those patients. For example, emergency room services may be more expensive to the patient and the provider. Further, patients often wait longer for services at an emergency room than they would need to wait if they sought services from urgent care or other service models. Significantly, patients with the same conditions often have worse outcomes when services are delivered at an emergency room than when they are delivered elsewhere. In view of the above, systems and methods for identifying patients who should seek alternatives to emergency room services are desirable. However, the complexity of analysis of healthcare provision and the constantly changing nature of healthcare makes it difficult or impossible to determine static rules or methods for identifying such patients. Rather, any such systems or methods must incorporate changing conditions and variations in patients and patient demographics. Thus, to address the problems above, a technical solution is desired that is dynamic and incorporates machine learning.

In view of the above technological challenges, systems and methods are desired for identifying patients predicted to benefit from redirection in health care services from emergency room services to other services. In existing techniques for identifying avoidable emergency room visits, static data models or manual analysis may be used. However, such approaches are error prone and inaccurate, and can lead to improper care or more expensive care.

The systems and methods described overcome known deficiencies in previous technological approaches. Specifically, by utilizing multiple algorithmic approaches, the healthcare prediction system is configured to utilize (a) a geospatial prevalence engine to identify at least one locally prevalent disease having associated locally prevalent disease symptoms; (b) a claims processing engine determine whether the patient is associated with at least one prior avoidable emergency room claim; (c) a health record engine to create a predictive model configured to determine whether the emergency room services request is associated with an avoidable visit; and (d) a score based approach to determine whether emergency room services requests are associated with avoidable visits.

Described herein are systems and methods that accordingly provide technological improvements to computers and computer systems used in medical and insurance systems by providing prediction based analyses. The prediction models described herein are configured to dynamically reevaluate data related to disease, medical claims, and healthcare records depending upon geographical region, time, and identifier to identify avoidable emergency room visits.

In one example, the systems and methods described are implemented using a healthcare prediction system for providing prediction based healthcare recommendations. The healthcare prediction system includes a first data warehouse system including a warehouse processor and a warehouse memory. In one example, the first data warehouse system further includes historical claims data. The historical claims data includes information related to claims for particular healthcare services including emergency room services, urgent care services, clinical services, and services from any other provider. As used herein, the term "alternative" or "alternate" refers to any service for healthcare that may be provided in lieu of emergency room services when such emergency room services are "avoidable". Therefore, in many examples, "alternative services" include those that may be provided as a substitute or alternate when emergency room services are "avoidable" or undesired because emergency room services are predicted to result in inferior treatment, worse outcomes, greater wait times, or higher costs than the alternative healthcare services. Thus, as used herein, "avoidable emergency room visits" refer to emergency room visits that can be avoided by substituting the visits for an alternative service without adverse impact to patient health or patient care.

In many examples, the first data warehouse system includes additional data used by the systems described herein including, without limitation, electronic medical records for patients, electronic health records for patients, information related to disease and disease treatments, and information related to care and triage of medical problems. The first data warehouse system is further configured to access and interact with other computer systems to obtain related data. In all examples, the healthcare prediction system is configured to store, provide, and utilize any electronic medical records, electronic health records, historical claims data, and any other data in a manner that is compliant with any applicable rules or statutes on patient privacy or individual privacy including the Health Insurance Portability and Accountability Act ("HIPAA").

The healthcare prediction system also includes a healthcare prediction server that is in communication with the first data warehouse system. The healthcare prediction server includes a processor and a memory. The processor is configured to receive an emergency room services request from a patient. In one example, the emergency room services request includes a requestor location, a requestor identifier, and requestor symptoms.

The emergency room services request represents a request by a patient considering an emergency room services visit. More specifically, in many examples, a patient indirectly interacts with the healthcare prediction system (and, more specifically the health care prediction server) to determine whether a planned or intended emergency room services visit is avoidable or whether an alternative service is recommended. In one example, the patient uses a patient computing device (e.g., a laptop, a desktop, a mobile device, a tablet device, or any other suitable device) to define an emergency room services request using an application that may be referred to as "emergency room avoidance application". In another example, the patient uses a computing device to define the emergency room services request using a browser based web application that may be referred to as an "emergency room avoidance portal". In a further example, the patient uses a suitable computing device (e.g., a mobile device) to define the emergency room services request using a mobile application ("app") that may be referred to as an "emergency room avoidance app". In another example, the patient uses a suitable computing device (e.g., a kiosk desktop device) provided by a healthcare provider (e.g., a hospital kiosk at or near an emergency room) to define the emergency room services request using any of the applications, portals, or apps referenced previously. The emergency room services request may be provided through any suitable means including a patient inputting underlying information including a requestor location (i.e., the location of the patient and/or the location where the patient seeks services), a requestor identifier (i.e., an identifier to specifically identify the patient and, in some examples, to reference relevant historical data associated with the patient and evaluation of whether the visit is avoidable), and requestor symptoms (i.e., a listing of symptoms that the patient identifies as relevant to the intended emergency room visit). In some examples, the app is configured to be presented to users based on their behavior and the location of the mobile computing device. For example, when a patient is near or proximate to an emergency room (e.g., within a vicinity of less than one thousand feet, or any suitable distance), a push notification may be sent to the mobile device of the patient to open the app, or any other suitable tool. In some examples, when a patient makes a selection based on the push notification, the app may open and partially define an emergency room services request based on at least the requestor location and requestor identifier, if such information is accessible from the mobile device. For example, the requestor location and requestor identifier may be included in a device profile that is accessible to the app. In some examples, the requestor location may also indicate the actual emergency room associated with the intended emergency room visit. In other examples, the emergency room services request may be determined based on information available at the patient computing device. For example, location data in the patient computing device may be used to populate the requestor location. Similarly, identification information in the patient computing device may be used to populate the requestor identifier. Further, the patient computing device may access or otherwise track patient symptoms (e.g., through a wellness application) and convey such information as requestor symptoms. In all examples, the healthcare prediction server receives the emergency room services request including such information. In some examples, the healthcare prediction server may receive more information with the emergency room services request including information related to patient availability and the reported urgency of the condition. Such information may be used to determine whether the emergency room visit is avoidable and how, if possible, to reschedule it as an alternative services request.

The healthcare prediction server is also configured to receive a first portion of the historical claims data from the data warehouse system. The first portion includes associated historical outcome data. Thereby, the healthcare prediction server receives information related to historical claims along with indications about the results of treatments associated with those historical claims. The historical claims data includes relevant information defining, for example, (a) the date and time of the claim; (b) the date and time of the associated service; (c) the location of the service; (d) the services type (e.g., emergency room, urgent care, clinic, other hospital, outpatient, or other); (e) information related to the underlying condition associated with the claim; (f) the claimant identifier; (g) costs incurred; (h) costs incurred by the claimant; (i) costs incurred by the provider; (j) costs incurred by the insurer; (k) timing information indicating the time the patient waited for the service; and (l) outcome data related to the patient after the service was provided. Outcome data may also be obtained, for example, by evaluating subsequent claimant for the same claimant and the same condition. In some examples, the first portion of the historical data is limited to relevant information based on, for example, time (e.g., the first portion is obtained for a relevant lookback period such as sixty or ninety days), geography (e.g., the first portion is obtained for a limited geographic region relevant to care, or limited to providers relevant to the emergency room services request such as providers within a geographic range of the emergency room indicated in the emergency room services request), provider (e.g., the first portion limited to providers relevant to the emergency room services request such as providers that provide care equivalent to the emergency room indicated in the emergency room services request), and claimant.

The healthcare prediction server is also configured to apply a geospatial prevalence engine to the first portion of the historical claims data and the requestor location to identify at least one locally prevalent disease having associated locally prevalent disease symptoms. Specifically, the healthcare prediction server utilizes disease information from sources including Centers for Disease Control ("CDC") databases, the National Institute of Health ("NIH") databases, or other suitable sources. In some examples, the first data warehouse system accesses and stores such disease information and the healthcare prediction server utilizes data from the first data warehouse system. In all examples, the geospatial prevalence engine processes the requestor location to identify locally prevalent diseases that a patient may be experiencing when they consider emergency services at the requestor location. Stated differently, the geospatial prevalence engine identifies locally prevalent diseases that may cause a patient to seek an emergency room at the location of the requestor location. The geospatial prevalence engine also may be configured to process the first portion of the historical claims data to validate that claimants at the requestor location have experienced the locally prevalent diseases indicated in the disease information records (i.e., those provided by the CDC or NIH databases). In some examples, such validation may be performed for a suitable time window to validate that such locally prevalent illnesses have been treated recently (e.g., within the past thirty days). By identifying and verifying such locally prevalent diseases that have been treated near or at the requestor location, the healthcare prediction server may allow identification of conditions suitable that, if they are the reason for an emergency room visit, justify avoidance of the emergency room because equivalent or superior care may be provided elsewhere.

The healthcare prediction server is also configured to apply a claims processing engine to the first portion of historical claims data and the requestor identifier to determine whether the patient is associated with at least one prior avoidable emergency room claim. More specifically, by comparing the historical claims data to the requestor identifier, the healthcare prediction server identifies claimants with a history of seeking emergency room services (e.g., at least one previous emergency room visit). If the outcome data indicates that the claimant previously sought emergency room services, the claims processing engine analyzes the associated claim(s) to determine whether prior visits were avoidable. In an example embodiment, information related to the underlying condition associated with the claim may be indicated by codes or classifications such as International Classification of Disease ("ICD") codes. The claims processing engine may process such codes or classifications to identify which codes are associated with avoidable emergency room visits. Determinations of avoidable visits may be made based on classification rules (e.g., ICD rules and specifications) or by comparing the historical claims data to associated outcome data. For example, historical claims data for similar conditions to those previously experienced by the claimant may be compared to determine if other claimants experience equivalent or better results when emergency room services were not used. Comparisons of such outcomes may be made using any suitable metric including, for example, healthcare outcome, time waited, and cost.

Upon determining at least one of a) that the patient is associated with at least one prior avoidable emergency room claim and b) that the requestor symptoms match the locally prevalent disease symptom, the healthcare prediction server is configured to predict that the emergency room services request is associated with an avoidable visit. Specifically, in the example embodiment, the healthcare prediction server is configured to determine whether a) the emergency room services request is associated with a claimant with a history of prior avoidable emergency room claims or b) the emergency room services request is associated with a claimant with symptoms that correspond to a locally prevalent disease that is present in the requestor location. In either case, the healthcare prediction server is configured to determine that the emergency room services visit is associated with an avoidable visit.

If the healthcare prediction server determines that the emergency room services visit is associated with an avoidable visit, the healthcare prediction server is also configured to transmit an alternative services request. The alternative services request is determined based on the requestor location, the requestor identifier, and the at least one symptom. Specifically, the healthcare prediction server is configured to identify an alternative services provider to assist the patient in resolving the conditions that underlie the emergency room services request, and to transmit a request for alternative services. In some examples, the alternative services request is presented to the patient (e.g., as an alert or notification indicating where an alternative service may be provided) directly to the patient computing device. In other examples, the alternative services request is transmitted (directly or indirectly) to the alternative services provider to initiate a setup of a request for such services. In other words, the healthcare prediction server may set up an actual appointment or consultation for a patient at an alternative services provider such as urgent care.

The healthcare prediction server is also configured to identify at least one alternative services provider to specify the alternative services request. In one example, the healthcare prediction server identifies potential providers within a defined geographic vicinity of the requestor location. The healthcare prediction server may identify potential providers by searching records of providers available in the first data warehouse system in the historic claim data or as a provider database. In any example, the healthcare prediction server can identify the geographic location of the requestor based on the requestor location and locations of alternative providers and identify possible providers within a reasonable range of the requestor location. In one example, the range is set by default (e.g., twenty miles) and in other examples the range may be set by the requestor in the emergency room services request. For example, the patient may specify how far they are willing to travel for an alternative provider. Similarly, the healthcare prediction server identifies potential providers that are possible valid providers based on, for example, the nature of services provided or the hours of operation. In some examples, alternative services providers are identified if and when they are operational or will be operational within a suitable time window defined by default or in the emergency room services request. In other examples, alternative services providers are identified if they provide services equivalent to those of the emergency room associated with the emergency room services request. Service listings may be provided in a provider database or in historic claim data.

As described, in some examples the healthcare prediction server is also configured to set appointments for alternative services. In such examples, the healthcare prediction server is also configured to identify at least one appointment window from the at least one alternative services provider by accessing a schedule interface or schedule database associated with the alternative services provider. The healthcare prediction server is also configured to transmit the alternative services request defined based on the requestor location, the requestor identifier, the at least one symptom, and the at least one alternative services provider.

In some examples, the healthcare prediction server is configured to create a predictive analytics model configured to provide a likelihood score that an emergency room services request is associated with an avoidable visit. The healthcare prediction server processes the first portion of the historical claims data and the associated historical outcome data to generate the predictive analytics model. Specifically, the healthcare prediction server analyzes previous historic claims data to identify avoidable emergency room visits based on outcome data. The predictive analytics model is generated by analyzing the historic claims data and outcome data to identify features of the historic claims data that determine whether an emergency room visit is avoidable. In the examples described, any suitable predictive model may be used including, for example, regression, linear regression, discrete choice, logistic regression, probit regression, multinomial logistic regression, logit regression, time series models, or any other suitable model. In the example embodiment, the predictive model may be generated using linear or logistic regression and thereby identify features that are likely to predict whether an emergency room visit is avoidable. The healthcare prediction server is also configured to apply the predictive analytics model to the emergency room services request to obtain the likelihood score that the emergency room services request is associated with an avoidable visit. Specifically, the healthcare prediction server applies available data from the emergency room services request to the predictive model and results in a scoring of likelihood of avoidability. In the example embodiment, the healthcare prediction server also determines thresholds for the score to set likelihoods that a given score indicates that an emergency room visit is avoidable. In the example embodiment, the thresholds are set using algorithms similar to those used to create the predictive model described above. Thus, a given score may indicate a given predictive confidence that an emergency room visit is avoidable. Upon determining that the likelihood score exceeds a first predetermined threshold indicating that the emergency room services request is associated with an avoidable visit, the healthcare prediction server is configured to transmit the alternative services request defined based on the requestor location, the requestor identifier, and the at least one symptom.

As described above, the healthcare prediction server may be configured to analyze historic claims data to identify features relevant to determining whether a particular emergency room services request is avoidable. In some embodiments described above, such features may be present in the emergency room services request from the beginning. In other examples, additional relevant features for the predictive model may increase the confidence of predicting whether an emergency room services visit is avoidable. Thus, the healthcare prediction server may seek further information from the patient to assist in that determination if a suitable confidence level is met by the healthcare prediction server to suggest that an emergency room services visit is avoidable. Practically, in such examples, the healthcare prediction server may prompt the patient (directly or indirectly) for further information about their request. For example, if a requestor symptom indicates a risk of a heart attack, the healthcare prediction server may prompt a patient for information including, "Where does your pain originate from?", "What is the severity of your pain?", "How long have you been experiencing your pain?", "Do you have shortness of breath?", "Do you have cold sweats or fatigue?", and "Do you have lightheadedness or dizziness?" (These examples are illustrative only and provided for clarity. In practice, such questions are determined based on historic claims data and relationships identified between the underlying features and the outcomes based on the algorithmic approaches described above.) Based on the predictive model, the responses to each supplemental question may be designated as a feature with an associated weight. The healthcare prediction server receives a supplemental emergency room services request responsive to the supplemental question(s) and rescores the likelihood that the emergency room visit is avoidable. Phrased differently, upon determining that the likelihood score exceeds a second predetermined threshold indicating that the emergency room services request is likely associated with an avoidable visit, the healthcare prediction server is configured to transmit at least one supplemental question to the patient. The healthcare prediction server is also configured to receive a supplemental emergency room services request in response to the at least one supplemental question. The healthcare prediction server is also configured to apply the predictive analytics model to the supplemental emergency room services request to obtain the likelihood score that the emergency room services request is associated with an avoidable visit. Upon determining that the likelihood score exceeds the first predetermined threshold indicating that the emergency room services request is associated with an avoidable visit, the healthcare prediction server is also configured to transmit the alternative services request defined based on the requestor location, the requestor identifier, and the at least one symptom.

In some examples, the healthcare prediction server is also configured to utilize electronic health records ("EHR") and electronic medical records ("EMR") to determine whether an emergency room visit is avoidable. The healthcare prediction server is configured to receive a second portion of electronic medical records and a third portion of electronic health records, wherein the second and third portions include associated historical outcome data from the data warehouse system. The healthcare prediction server is also configured to apply a health record engine to the second portion of a plurality of electronic medical records and the third portion of electronic health records to create a predictive model configured to determine whether the emergency room services request is associated with an avoidable visit. The healthcare prediction server is further configured to apply the predictive model to the emergency room services request to determine whether the emergency room services request is associated with an avoidable visit. Upon determining that the emergency room services request is associated with an avoidable visit, the healthcare prediction server is configured to transmit the alternative services request defined based on the requestor location, the requestor identifier, and the at least one symptom. Thus, the healthcare prediction server utilizes the health record engine to identify relevant features in EHR and EMR records indicating that an emergency room visit is avoidable, to generate an associated predictive model, and to apply the predictive model to the emergency room services request to determine whether the emergency room services request is associated with an avoidable visit. This approach allows the healthcare prediction server to utilize EHR and EMR data to make the determination on avoidability of emergency room visits. In some example, the healthcare prediction server can utilize the first, second, and third portions of data and create a model based on historic claims data, EHR data, and EMR data.

The healthcare prediction server is also configured to refine the predictive model as needed. For example, the healthcare prediction server can refine the predictive models described by, for example, constraining location data associated with the EMR and EHR data to create a location based predictive model. Similarly, the healthcare prediction server can constrain claims data by location to create a location based predictive model from claims data, or to create a location based predictive model from claims data, EHR data, and EMR data. In other examples, the data underlying the predictive models may be constrained by other variables including time, symptom, and any other suitable classification to create other constrained predictive models.

In another example, the healthcare prediction server is configured to process the second portion of a plurality of electronic medical records and the third portion of electronic health records into associated descriptive and diagnostic records. Specifically, the healthcare prediction server processes the EHR and EMR records to obtain descriptive and diagnostic records that describe, for example, individual healthcare events. In such examples, the healthcare prediction server applies the health record engine to the descriptive and diagnostic records to create the predictive model configured to determine whether the emergency room services request is associated with an avoidable visit. In other similar examples, the healthcare prediction server may pre-process other records (e.g., claims records) to obtain similar descriptive records before creating an associated predictive model.

Generally, the systems and methods described herein are configured to perform at least the following steps: receiving an emergency room services request from a patient, the emergency room services request including a requestor location, a requestor identifier, and requestor symptoms; receiving a first portion of the plurality of historical claims data from the data warehouse system, wherein the first portion includes associated historical outcome data; applying a geospatial prevalence engine to the first portion of the plurality of historical claims data and the requestor location to identify at least one locally prevalent disease having associated locally prevalent disease symptoms; applying a claims processing engine to the first portion of the plurality of historical claims data and the requestor identifier to determine whether the patient is associated with at least one prior avoidable emergency room claim; upon determining at least one of a) that the patient is associated with at least one prior avoidable emergency room claim and b) that the requestor symptoms match the locally prevalent disease symptom, predicting that the emergency room services request is associated with an avoidable visit; transmitting an alternative services request defined based on the requestor location, the requestor identifier, and the at least one symptom; identifying at least one alternative services provider by identifying potential providers within a defined geographic vicinity of the requestor location; identifying at least one appointment window from the at least one alternative services provider; transmitting the alternative services request defined based on the requestor location, the requestor identifier, the at least one symptom, and the at least one alternative services provider; creating a predictive analytics model configured to provide a likelihood score that an emergency room services request is associated with an avoidable visit by processing the first portion of the plurality of historical claims data and the associated historical outcome data; applying the predictive analytics model to the emergency room services request to obtain the likelihood score that the emergency room services request is associated with an avoidable visit; upon determining that the likelihood score exceeds a first predetermined threshold indicating that the emergency room services request is associated with an avoidable visit, transmitting the alternative services request defined based on the requestor location, the requestor identifier, and the at least one symptom; upon determining that the likelihood score exceeds a second predetermined threshold indicating that the emergency room services request is likely associated with an avoidable visit, transmitting at least one supplemental question to the patient; receiving a supplemental emergency room services request in response to the at least one supplemental question; applying the predictive analytics model to the supplemental emergency room services request to obtain the likelihood score that the emergency room services request is associated with an avoidable visit; upon determining that the likelihood score exceeds the first predetermined threshold indicating that the emergency room services request is associated with an avoidable visit, transmitting the alternative services request defined based on the requestor location, the requestor identifier, and the at least one symptom; receiving a second portion of a plurality of electronic medical records and a third portion of electronic health records, wherein the second and third portions include associated historical outcome data from the data warehouse system; applying a health record engine to the second portion of a plurality of electronic medical records and the third portion of electronic health records to create a predictive model configured to determine whether the emergency room services request is associated with an avoidable visit; applying the predictive model to the emergency room services request to determine whether the emergency room services request is associated with an avoidable visit; upon determining that the emergency room services request is associated with an avoidable visit, transmitting the alternative services request defined based on the requestor location, the requestor identifier, and the at least one symptom; refining the predictive model based on location data associated with the second portion of a plurality of electronic medical records and the third portion of electronic health records to create a location based predictive model; processing the second portion of a plurality of electronic medical records and the third portion of electronic health records into associated descriptive and diagnostic records; applying the health record engine to the descriptive and diagnostic records to create the predictive model configured to determine whether the emergency room services request is associated with an avoidable visit.

FIG. 1 is a functional block diagram of an example insurance claim processing system 100 including a primary insurance processor system 110. Primary insurance processor system 110 includes subsystems 112, 114, and 116 capable of providing claim processing, claim adjudication, and claim payment respectively. Specifically, primary insurance processor system 110 is associated with a corresponding primary insurance database system 120. As described above and herein, database systems such as database systems 120 may include one or more than one databases that each are configured to use a DBMS. In some cases the DBMS systems may be distinct from one another. Further, each database is associated with a data schema that may be unique depending on whether the DBMS and claim category are distinct. As such, the databases include data that cannot be processed using common programs. Database systems 120 include necessary information stored on at least one of their underlying databases. Specifically, primary insurance database system 120 includes coverage data 122, claim data 124, and payment data 126.

Figure 2:
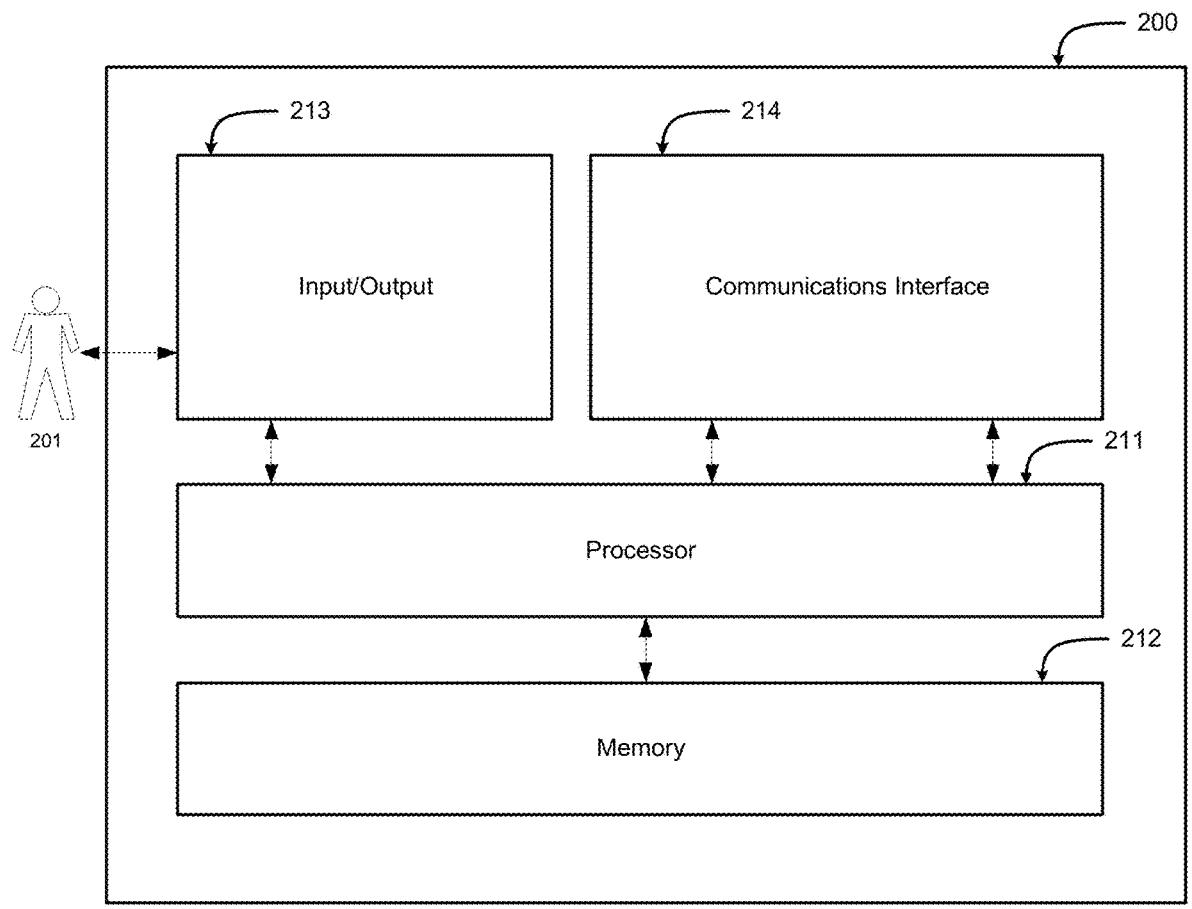
FIG. 2 is a functional block diagram of an example computing device that may be used in the healthcare prediction system described.
Figure 3:
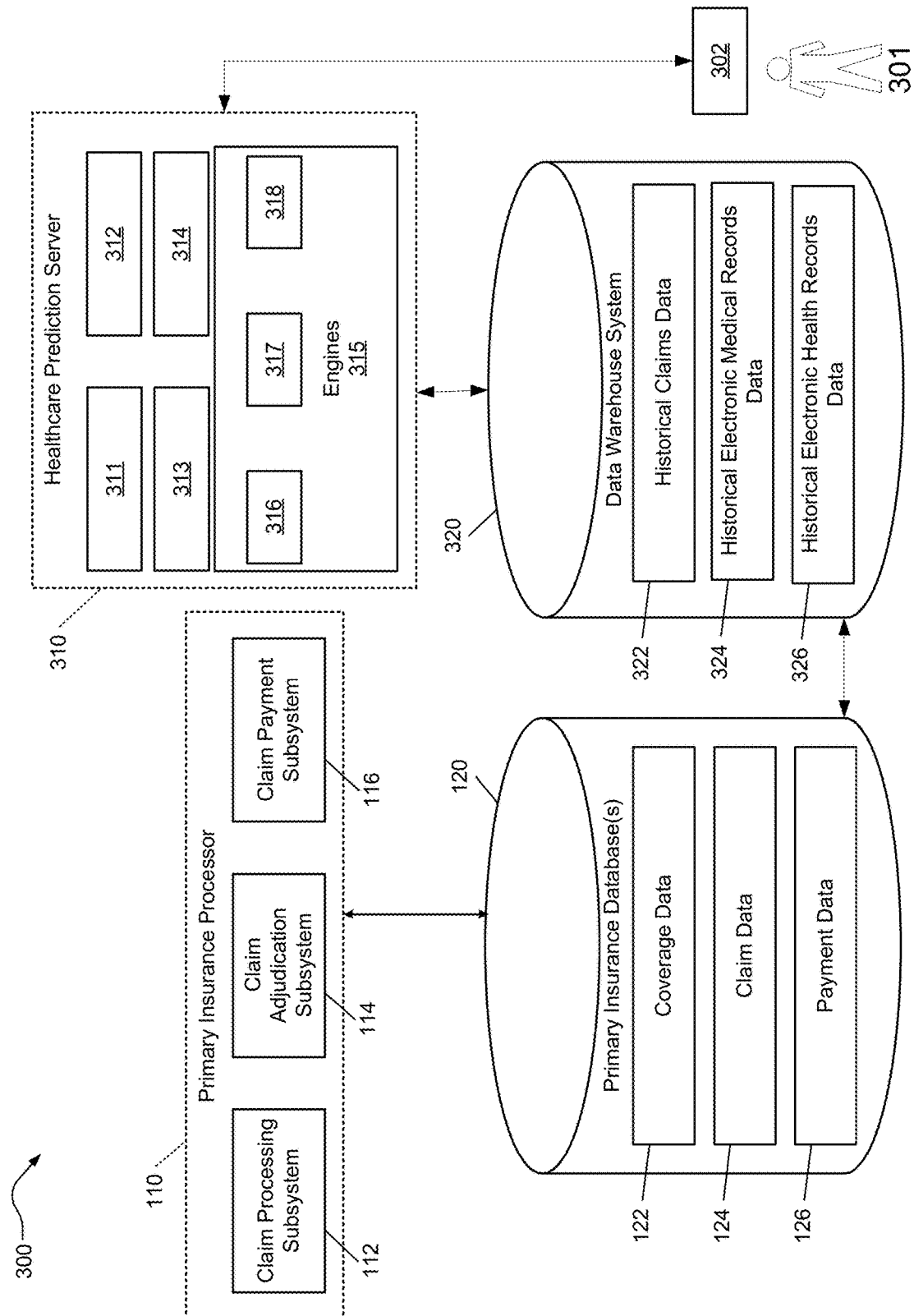
FIG. 3 is a functional block diagram of a healthcare prediction system that may be deployed within the system of FIG. 1 using the computing devices shown in FIG. 2.

FIG. 2 is a functional block diagram of an example computing device that may be used in the prediction based healthcare recommendation method described, and may represent the healthcare prediction server and/or data warehouse system (all shown in FIG. 3). Specifically, computing device 200 illustrates an example configuration of a computing device for the systems shown herein, and particularly in FIGS. 1 and 3. Computing device 200 illustrates an example configuration of a computing device operated by a user 201 in accordance with one embodiment of the present invention. Computing device 200 may include, but is not limited to, the healthcare prediction server and/or data warehouse system (all shown in FIG. 3), other user systems, and other server systems. Computing device 200 may also include servers, desktops, laptops, mobile computing devices, stationary computing devices, computing peripheral devices, smart phones, wearable computing devices, medical computing devices, and vehicular computing devices. In some variations, computing device 200 may be any computing device capable of the described healthcare prediction and recommendation methods. In some variations, the characteristics of the described components may be more or less advanced, primitive, or non-functional.

In an example embodiment, computing device 200 includes a processor 211 for executing instructions. In some embodiments, executable instructions are stored in a memory area 212. Processor 211 may include one or more processing units, for example, a multi-core configuration. Memory area 212 is any device allowing information such as executable instructions and/or written works to be stored and retrieved. Memory area 212 may include one or more computer readable media.

Computing device 200 also includes at least one input/output component 213 for receiving information from and providing information to user 201. In some examples, input/output component 213 may be of limited functionality or non-functional as in the case of some wearable computing devices. In other examples, input/output component 213 is any component capable of conveying information to or receiving information from user 201. In some embodiments, input/output component 213 includes an output adapter such as a video adapter and/or an audio adapter. Input/output component 213 may alternatively include an output device such as a display device, a liquid crystal display (LCD), organic light emitting diode (OLED) display, or "electronic ink" display, or an audio output device, a speaker or headphones. Input/output component 213 may also include any devices, modules, or structures for receiving input from user 201. Input/output component 213 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 213. Input/output component 213 may further include multiple sub-components for carrying out input and output functions.

Computing device 200 may also include a communications interface 214, which may be communicatively coupleable to a remote device such as a remote computing device, a remote server, or any other suitable system. Communication interface 214 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 214 is configured to allow computing device 200 to interface with any other computing device or network using an appropriate wireless or wired communications protocol such as, without limitation, BLUETOOTH®, Ethernet, or IEEE 802.11. Communications interface 214 allows computing device 200 to communicate with any other computing devices with which it is in communication or connection.

FIG. 3 is a functional block diagram of a healthcare prediction system 300 that may be deployed within the system 100 (shown in FIG. 1) using the computing devices 200 (shown in FIG. 2.) In one example, healthcare prediction system 300 includes primary insurance processor 110 (along with associated subsystems 112, 114, 116) and primary insurance database(s) 120 (along with associated data 122, 124, and 126). Healthcare prediction system 300 includes healthcare prediction server 310 which further includes processor 311, memory 312, input/output component 313, and communications interface 314. Healthcare prediction server 310 also includes engines 315 configured to perform the functions described herein. Specifically, engines 315 include geospatial prevalence engine 316, claims processing engine 317, and health record engine 318. Healthcare prediction system 300 also includes data warehouse system 320 which further includes, provides, and/or has access to historic claims data 322, historic EMR records data 324, and historic EHR records data 326. In the example embodiment, a patient 301 accesses healthcare prediction system 310 directly or indirectly using patient computing device 302 which facilitates the communication described herein.

As described above, geospatial prevalence engine 316 is applied first portion of the historical claims data and the requestor location to identify at least one locally prevalent disease having associated locally prevalent disease symptoms. Specifically, the healthcare prediction server 310 utilizes disease information from sources including Centers for Disease Control ("CDC") databases, the National Institute of Health ("NIH") databases, or other suitable sources. Thus, in some examples healthcare prediction server 310 receives such data from these databases through a network connection (not shown). In other examples, the first data warehouse system 320 accesses and stores such disease information and the healthcare prediction server 310 utilizes data from the first data warehouse system 320. In all examples, the geospatial prevalence engine 316 processes the requestor location to identify locally prevalent diseases that a patient may be experiencing when they consider emergency services at the requestor location.

The healthcare prediction server 310 is also configured to apply a claims processing engine 317 to the first portion of historical claims data 322 and the requestor identifier to determine whether the patient is associated with at least one prior avoidable emergency room claim. More specifically, by comparing the historical claims data 322 to the requestor identifier, the healthcare prediction server identifies claimants with a history of seeking emergency room services (e.g., at least one previous emergency room visit). If the outcome data indicates that the claimant previously sought emergency room services, the claims processing engine 317 analyzes the associated claim(s) to determine whether prior visits were avoidable. In an example embodiment, information related to the underlying condition associated with the claim may be indicated by codes or classifications such as International Classification of Disease ("ICD") codes. The claims processing engine 317 may process such codes or classifications to identify which codes are associated with avoidable emergency room visits. Determinations of avoidable visits may be made based on classification rules (e.g., ICD rules and specifications) or by comparing the historical claims data to associated outcome data. For example, historical claims data for similar conditions to those previously experienced by the claimant may be compared to determine if other claimants experience equivalent or better results when emergency room services were not used. Comparisons of such outcomes may be made using any suitable metric including, for example, healthcare outcome, time waited, and cost.

The healthcare prediction server 310 is also configured to apply a health record engine 318 to the second portion of a plurality of electronic medical records 324 and the third portion of electronic health records 326 to create a predictive model configured to determine whether the emergency room services request is associated with an avoidable visit. The healthcare prediction server 310 is further configured to apply the predictive model to the emergency room services request to determine whether the emergency room services request is associated with an avoidable visit. Upon determining that the emergency room services request is associated with an avoidable visit, the healthcare prediction server 310 is configured to transmit the alternative services request defined based on the requestor location, the requestor identifier, and the at least one symptom. Thus, the healthcare prediction server 310 utilizes the health record engine to identify relevant features in EHR and EMR records indicating that an emergency room visit is avoidable, to generate an associated predictive model, and to apply the predictive model to the emergency room services request to determine whether the emergency room services request is associated with an avoidable visit.

Figure 4:
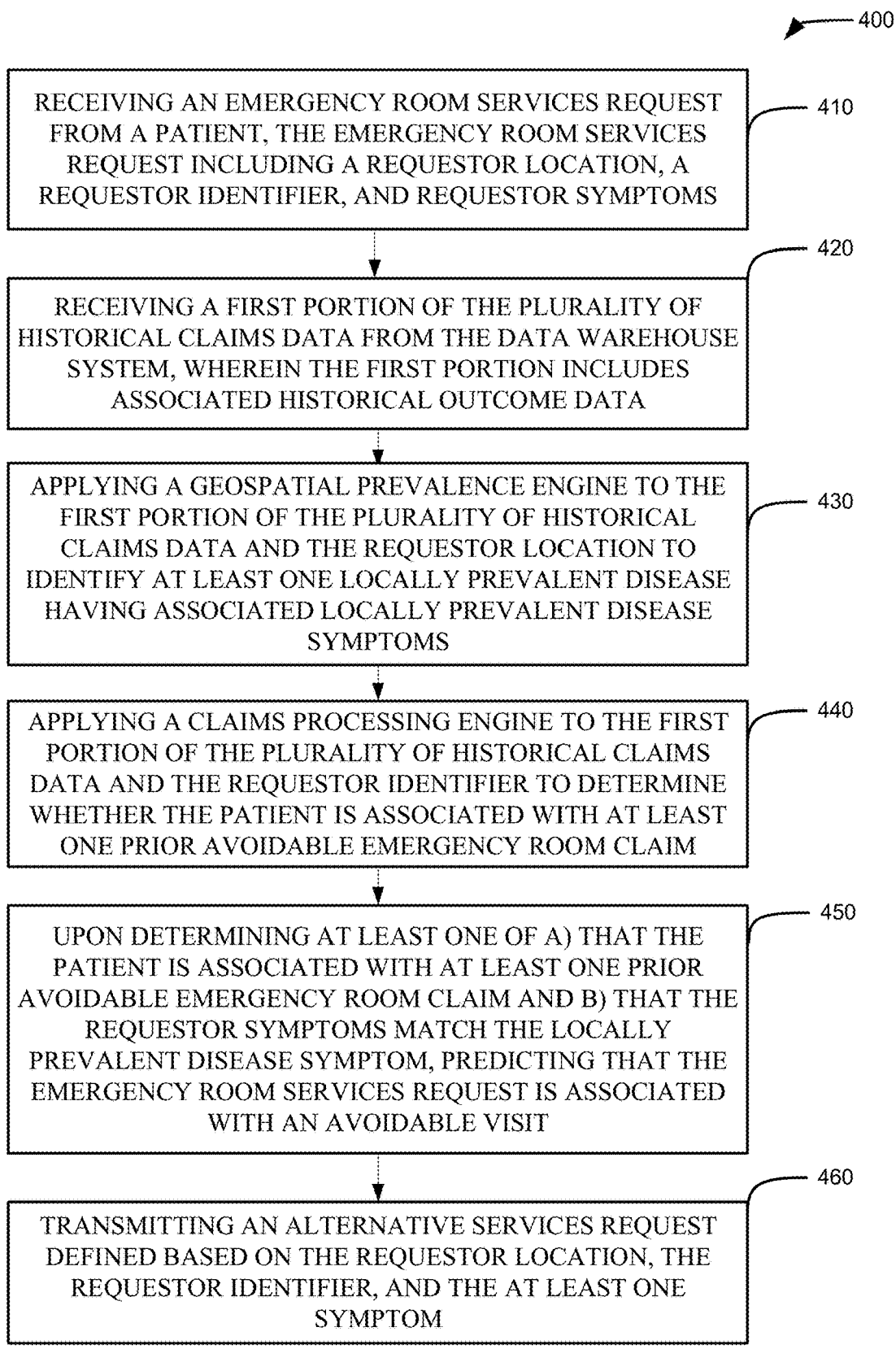
FIG. 4 is a flow diagram representing an example healthcare prediction and recommendation method from the perspective of the healthcare prediction server shown in FIG. 3.

FIG. 4 is a flow diagram 400 representing an example healthcare prediction and recommendation method from the perspective of the healthcare prediction server 310 (shown in FIG. 3). Healthcare prediction server 310 is configured to receive 410 an emergency room services request from a patient, the emergency room services request including a requestor location, a requestor identifier, and requestor symptoms. Healthcare prediction server 310 is also configured to receive 420 a first portion of the plurality of historical claims data from the data warehouse system, wherein the first portion includes associated historical outcome data. Healthcare prediction server 310 is further configured to apply 430 a geospatial prevalence engine to the first portion of the plurality of historical claims data and the requestor location to identify at least one locally prevalent disease having associated locally prevalent disease symptoms. Healthcare prediction server 310 is also configured to apply 440 a claims processing engine to the first portion of the plurality of historical claims data and the requestor identifier to determine whether the patient is associated with at least one prior avoidable emergency room claim. Upon determining at least one of a) that the patient is associated with at least one prior avoidable emergency room claim and b) that the requestor symptoms match the locally prevalent disease symptom, healthcare prediction server 310 is configured to predict 450 that the emergency room services request is associated with an avoidable visit. Healthcare prediction server 310 is configured to transmit 460 an alternative services request defined based on the requestor location, the requestor identifier, and the at least one symptom.

Figure 5:
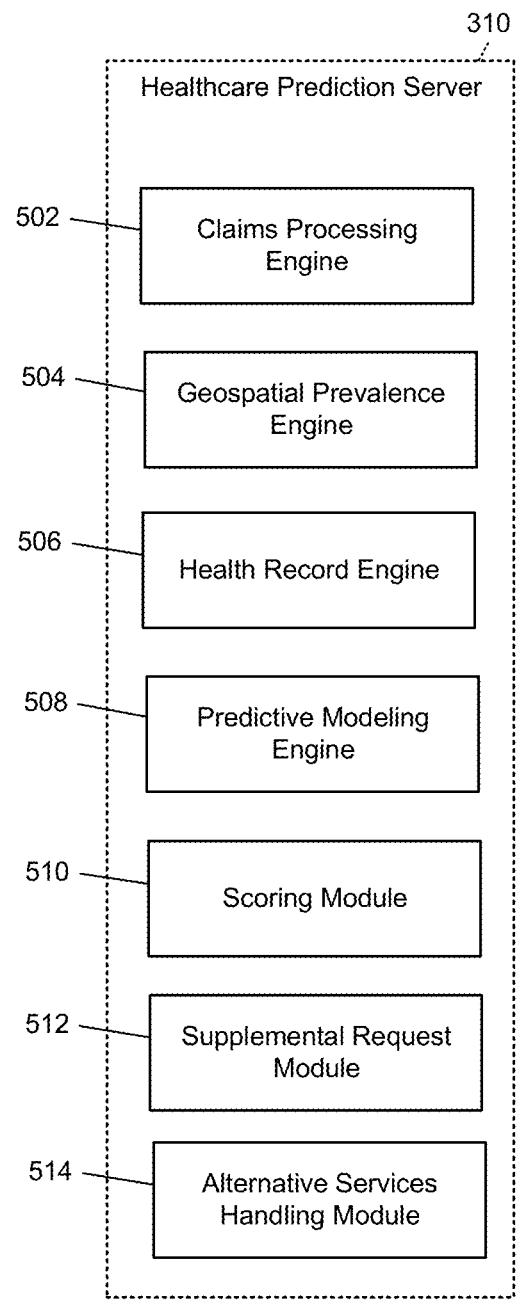
FIG. 5 is a diagram of elements of one or more example computing devices that may be used in the system shown in FIGS. 1 and 3.

FIG. 5 is a diagram of elements 502, 504, 506, 508, 510, 512, and 514 of one or more example computing devices that may be used in the system 300 (shown in FIG. 3). Healthcare prediction server 310 includes claims processing engine 502, geospatial prevalence engine 504, and health record engine 506, each of which are configured to perform the functions related to determining whether a particular emergency room visit is avoidable and to create related predictive models in the determination thereof. Healthcare prediction server 310 also includes predictive modeling engine 508 which defines the algorithmic approaches and methods taken for creating and defining predictive models ad described herein including, for example, defining which algorithms are utilized. Healthcare prediction server also includes scoring module 510 which is used for weighted scoring in conjunction with the claims processing engine 502 to make determinations regarding whether an emergency room visit is avoidable and/or if supplemental emergency room services request information is needed. Healthcare prediction server also includes supplemental request module 512 to define supplemental questions and to process supplemental emergency room services responses. Healthcare prediction server also includes alternative services handling module 514 which defines alternative service communications, processing, and routing.

Figure 6:
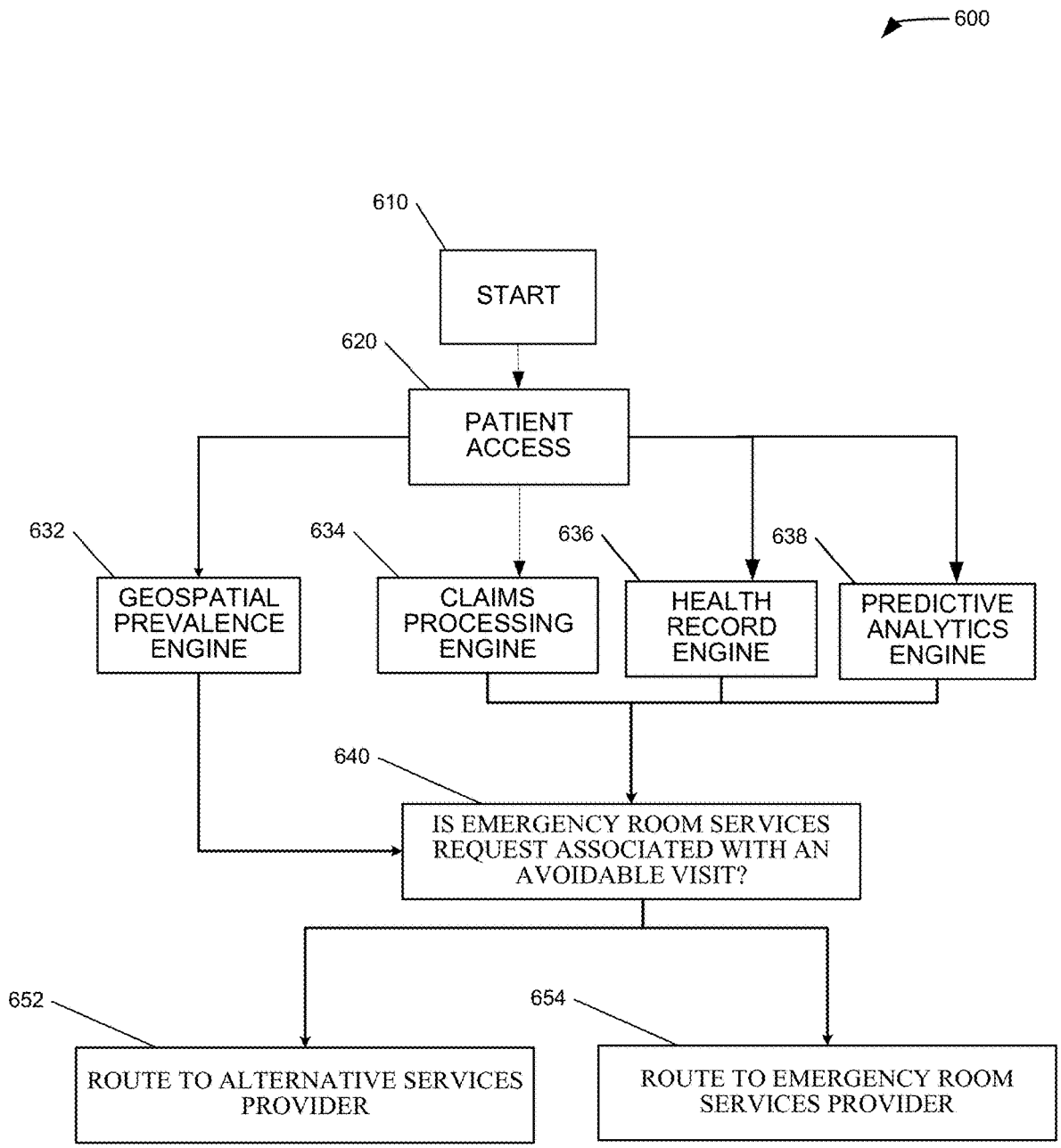
FIG. 6 is a flow diagram of an example healthcare prediction and recommendation method from the perspective of the healthcare prediction server shown in FIG. 3.

FIG. 6 is a flow diagram 600 of an example healthcare prediction and recommendation method from the perspective of the healthcare prediction server 310 (shown in FIG. 3). In the example embodiment, a process is initiated 610 and a patient (or other related user) accesses 620 the healthcare prediction server 310 (directly or indirectly) by using a patient computing device to interact with a portal, application, mobile app, or other suitable interface with healthcare prediction server 310 and submitting an emergency room services request. Depending upon the approach taken, healthcare prediction server 310 executes geospatial prevalence engine 632, claims processing engine 634, health record engine 636, and/or any other predictive analytics engine 638 to determine 640 whether an emergency room services request is associated with an avoidable visit. If the healthcare prediction server 310 determines 640 that the emergency room visit is avoidable a request is routed or transmitted 652 to an alternative services provider. If the healthcare prediction server 310 determines 640 that the emergency room visit is not avoidable a request is routed or transmitted 654 to an emergency room services provider.

Figure 7:
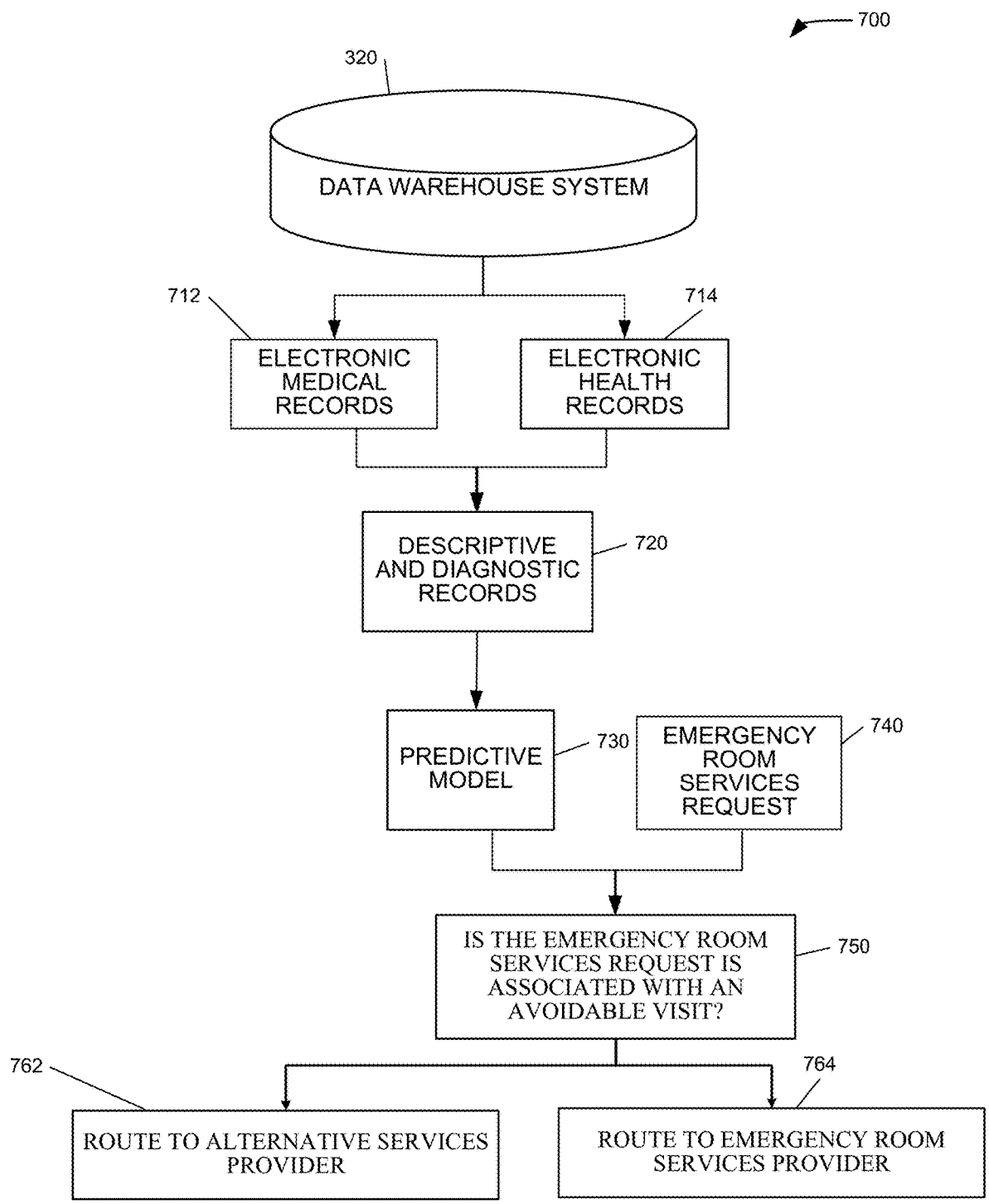
FIG. 7 is a flow diagram of an example healthcare prediction and recommendation method performed by the health record engine of the healthcare prediction server shown in FIG. 3.

FIG. 7 is a flow diagram 700 of an example healthcare prediction and recommendation method performed by the health record engine 318 of the healthcare prediction server 310 (shown in FIG. 3). Healthcare prediction server 310 receives EMR 712 and EHR 714 records from data warehouse system 320 or from any suitable system in communication with healthcare prediction server 310. Healthcare prediction server 310 processes EMR 712 and EHR 714 to obtain descriptive and diagnostic records 720. Healthcare prediction server 310 applies health record engine 318 to descriptive and diagnostic records 720, as described above, to obtain predictive model 730. Healthcare prediction server 310 applies emergency room services request 740 to predictive model 730 to determine 750 whether an emergency room services request is associated with an avoidable visit. If the healthcare prediction server 310 determines 750 that the emergency room visit is avoidable a request is routed or transmitted 762 to an alternative services provider. If the healthcare prediction server 310 determines 750 that the emergency room visit is not avoidable a request is routed or transmitted 764 to an emergency room services provider.

Figure 8:
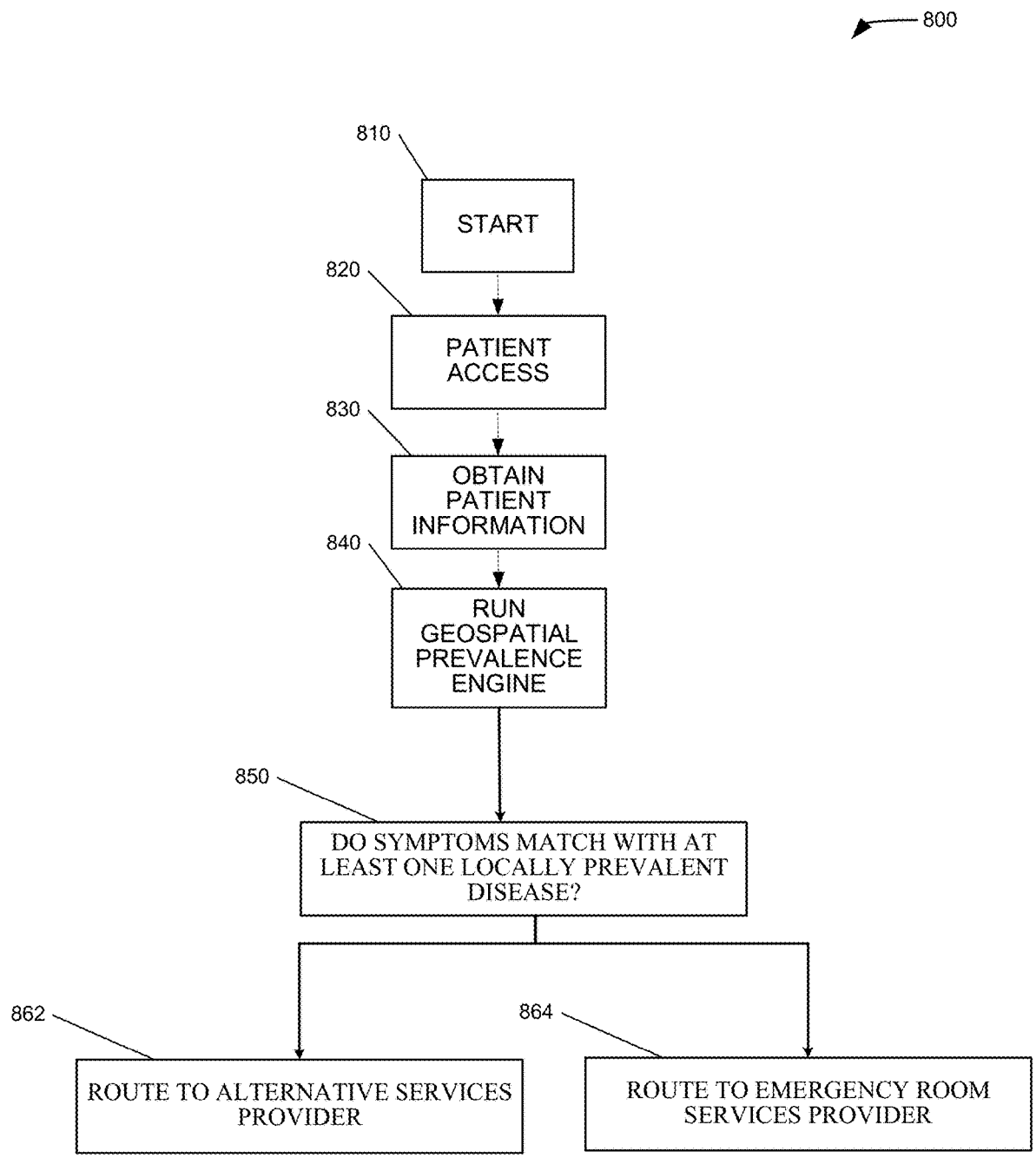
FIG. 8 is a flow diagram of an example healthcare prediction and recommendation method performed by the geospatial prevalence engine of the healthcare prediction server shown in FIG. 3.

FIG. 8 is a flow diagram 800 of an example healthcare prediction and recommendation method performed by the geospatial prevalence engine 316 of the healthcare prediction server 310 (shown in FIG. 3). In the example embodiment, a process is initiated 810 and a patient (or other related user) accesses 820 the healthcare prediction server 310 (directly or indirectly) by using a patient computing device to interact with a portal, application, mobile app, or other suitable interface with healthcare prediction server 810 and submitting an emergency room services request. Healthcare prediction server 310 obtains 830 patient information from the emergency room services request and healthcare prediction server 310 runs 840 geospatial prevalence engine 316 on the emergency room services request as described above to determine 850 whether the symptoms of the emergency room services request match at least one locally prevalent disease. If the healthcare prediction server 310 determines 850 that the symptoms of the emergency room services request match at least one locally prevalent disease, the healthcare prediction server 310 routes or transmits a request 862 to an alternative services provider. If the healthcare prediction server 310 determines 850 that the symptoms of the emergency room services request do not match at least one locally prevalent disease, the healthcare prediction server 310 routes or transmits a request 864 to an emergency room services provider.

Figure 9:
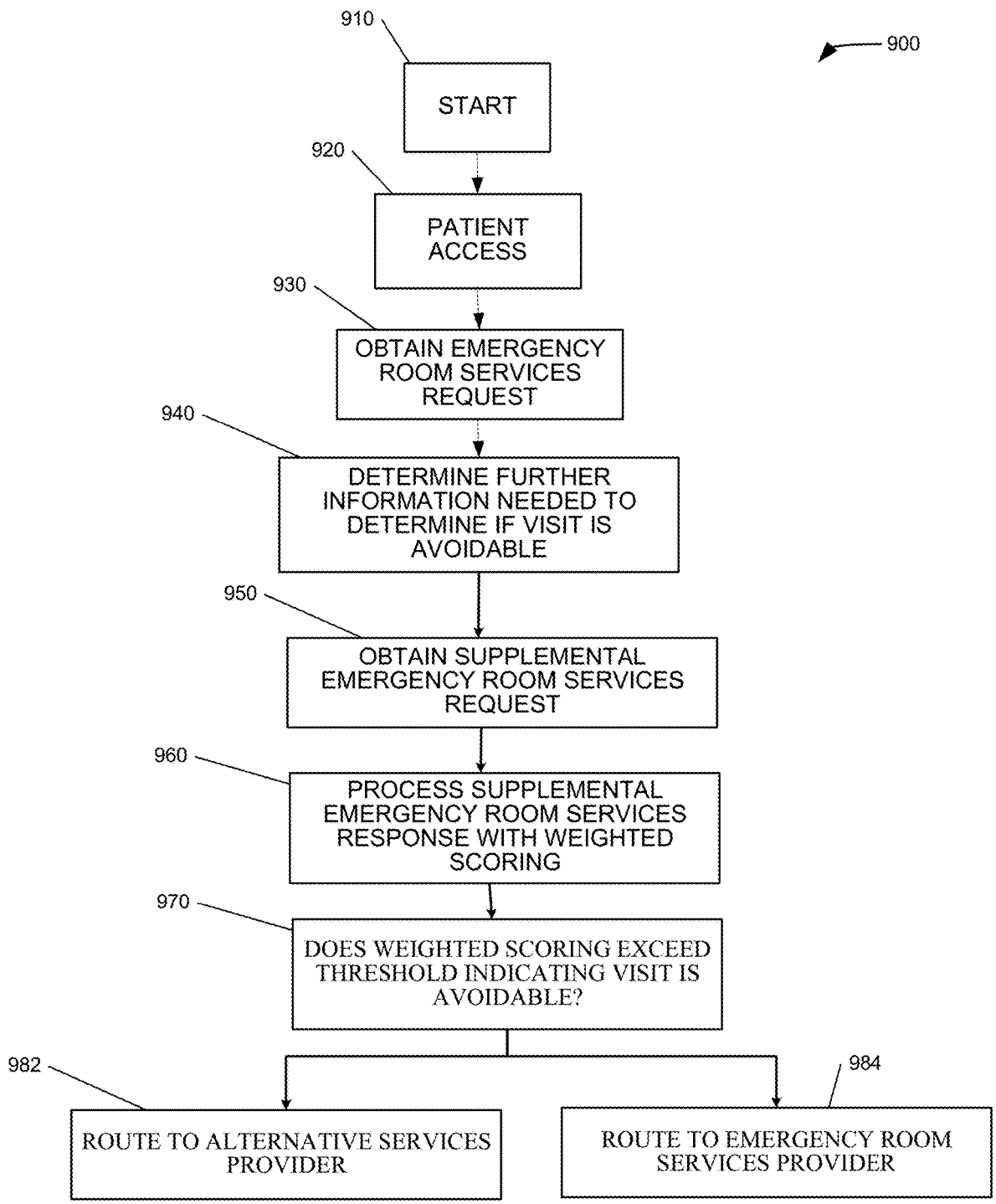
FIG. 9 is a flow diagram of an example healthcare prediction and recommendation method for performing a weighted scoring model to determine if the emergency room services request and supplemental emergency room services request indicate that the associated visit is avoidable, performed by the healthcare prediction server shown in FIG. 3.

FIG. 9 is a flow diagram 900 of the healthcare prediction and recommendation method for performing a weighted scoring model to determine if the emergency room services request and supplemental emergency room services request indicate that the associated visit is avoidable, performed by the healthcare prediction server 310 (shown in FIG. 3). In the example embodiment, a process is initiated 910 and a patient (or other related user) accesses 920 the healthcare prediction server 310 (directly or indirectly) by using a patient computing device to interact with a portal, application, mobile app, or other suitable interface with healthcare prediction server 310 and submitting an emergency room services request. Healthcare prediction server 310 obtains 930 patient information from the emergency room services request and healthcare prediction server 310. Healthcare prediction server 310 determines 940 if further information is needed to determine whether the related emergency room visit is avoidable. In the example embodiment, this determination 940 is made using the predictive model generated by the claims processing engine if application of the predictive model to the emergency room services request determines that further information is needed (i.e., supplemental responses) to determine whether the emergency room visit is avoidable. Healthcare prediction server 310 receives or obtains 950 a supplemental emergency room services response and applies 960 weighted scoring (defined by the predictive model) to determine 970 whether the weighted score exceeds a threshold indicating that an emergency room visit is avoidable. If the healthcare prediction server 310 determines 970 that the threshold is exceeded, the healthcare prediction server 310 routes or transmits a request 982 to an alternative services provider. If the healthcare prediction server 310 determines 970 that the threshold is not exceeded, the healthcare prediction server 310 routes or transmits a request 984 to an emergency room services provider.

The methods and systems (e.g., the healthcare prediction server 310) described herein can further train the predictive models using first data collected from the health records over a first time period, and validating the trained models using second data collected from the health records over a second time period. The first time period is longer in duration and older than the second time period.

The methods and systems (e.g., the healthcare prediction server 310) described herein can further train the validated models using the first data and the second data, and generating the predictions using the trained validated models.

The methods and systems (e.g., the healthcare prediction server 310) described herein can further include reconfiguring one of the models in response to the one of the models failing validation, retraining all of the models including the reconfigured model using the first data, and revalidating, subsequent to the retraining, all of the models including the reconfigured model using the second data.

Figure 10:
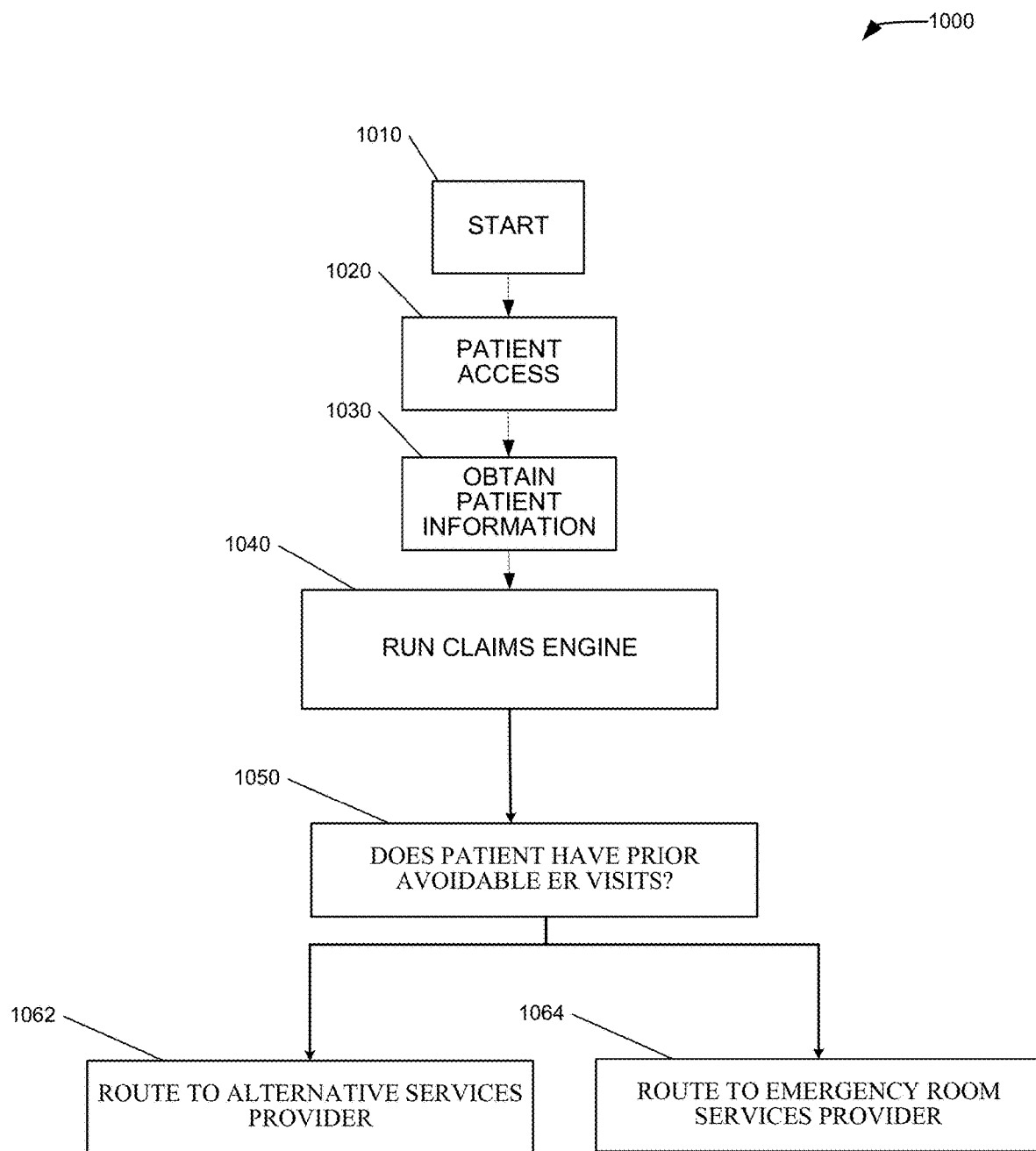
FIG. 10 is a flow diagram of an example healthcare prediction and recommendation method performed by the claims processing engine of the healthcare prediction server shown in FIG. 3.

FIG. 10 is a flow diagram 1000 of the healthcare prediction and recommendation method performed by the claims processing engine 317 of the healthcare prediction server 310 (shown in FIG. 3). In the example embodiment, a process is initiated 1010 and a patient (or other related user) accesses 1020 the healthcare prediction server 310 (directly or indirectly) by using a patient computing device to interact with a portal, application, mobile app, or other suitable interface with healthcare prediction server 310 and submitting an emergency room services request. Healthcare prediction server 310 obtains 1030 patient information from the emergency room services request and healthcare prediction server 310. Healthcare prediction server 310 applies 1040 claims processing engine 317 to determine whether the related emergency room visit is avoidable based on prior history of a claimant and emergency room visits. Specifically, the healthcare prediction server 310 is also configured to apply claims processing engine 317 to the first portion of historical claims data and the requestor identifier to determine whether the patient is associated with at least one prior avoidable emergency room claim. More specifically, by comparing the historical claims data to the requestor identifier, the healthcare prediction server 310 identifies claimants with a history of seeking emergency room services (e.g., at least one previous emergency room visit). If the outcome data indicates that the claimant previously sought emergency room services, the claims processing engine 317 analyzes the associated claim(s) to determine whether prior visits were avoidable. In an example embodiment, information related to the underlying condition associated with the claim may be indicated by codes or classifications such as International Classification of Disease ("ICD") codes. The claims processing engine 317 may process such codes or classifications to identify which codes are associated with avoidable emergency room visits. Determinations of avoidable visits may be made based on classification rules (e.g., ICD rules and specifications) or by comparing the historical claims data to associated outcome data. For example, historical claims data for similar conditions to those previously experienced by the claimant may be compared to determine if other claimants experience equivalent or better results when emergency room services were not used. Comparisons of such outcomes may be made using any suitable metric including, for example, healthcare outcome, time waited, and cost. The healthcare prediction server 310 determines 1050 that the patient has prior avoidable emergency room visits, the healthcare prediction server 310 routes or transmits a request 1062 to an alternative services provider. If the healthcare prediction server 310 determines 1050 that the patient does not have prior avoidable emergency room visits, the healthcare prediction server 310 routes or transmits a request 1064 to an emergency room services provider.

Figure 11:
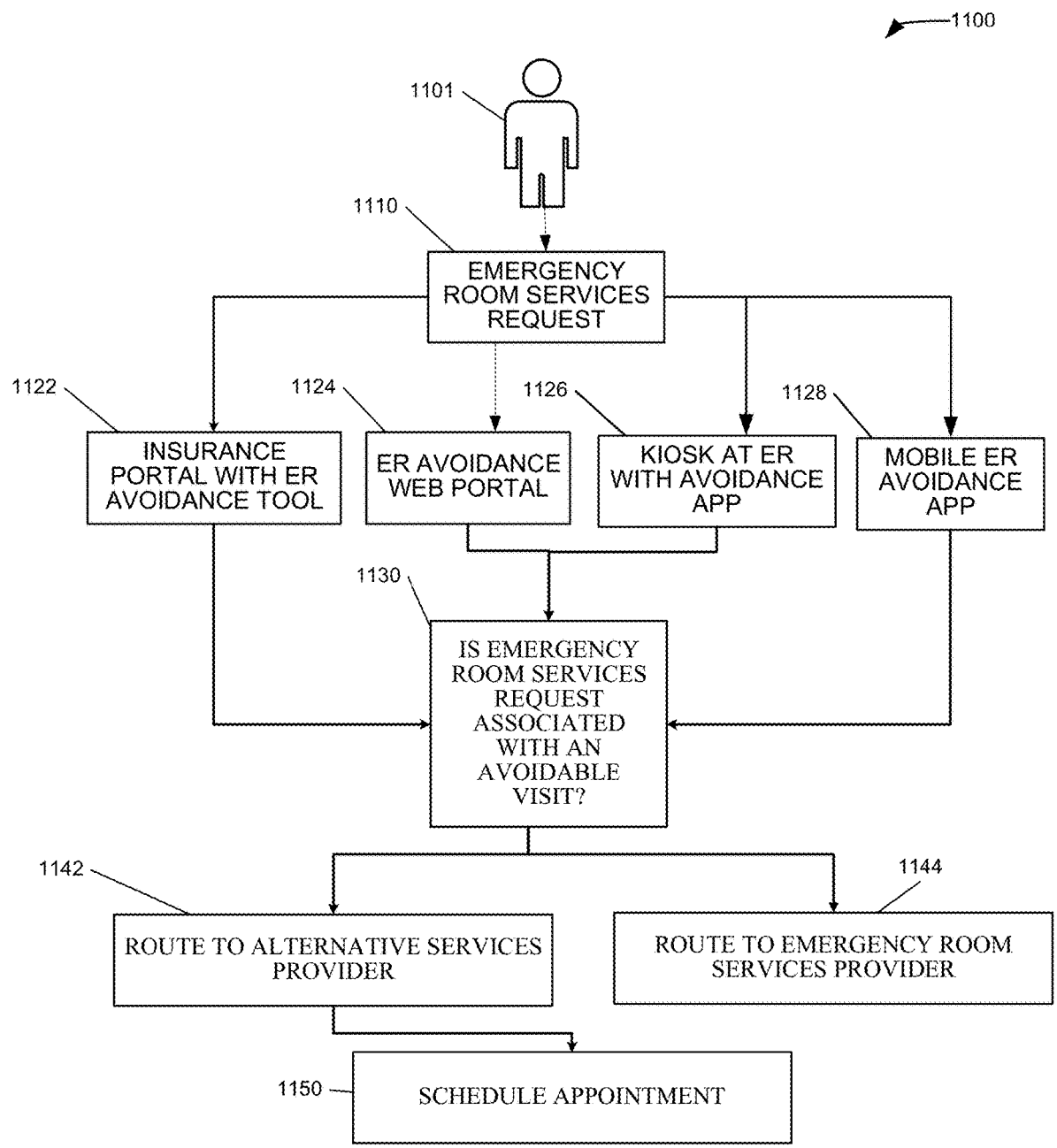
FIG. 11 is a system flow diagram of a user using the healthcare prediction system shown in FIG. 3.

FIG. 11 is a system flow diagram 1100 of a user 1101 using the healthcare prediction server 310 (shown in FIG. 3). Patient 1101 accesses a patient computing device to provide an emergency room services request 1110 through any suitable method including an insurance portal with an emergency room avoidance tool 1122, an emergency room avoidance web portal 1124, a kiosk at an emergency room with an avoidance app 1126, and a mobile emergency room avoidance app 1128. In some examples, the tools 1122, 1124, 1126, and 1128 are configured to be presented to users based on their behavior. For example, when a patient is near or proximate to an emergency room (e.g., within a vicinity of less than one thousand feet, or any suitable distance), a push notification may be sent to a mobile device of the patient to open tools 1122, 1124, 1126, 1128, or any other suitable tool. In some examples, when a patient makes a selection based on the push notification, tools 1122, 1124, 1126, and 1128 may open and partially define an emergency room services request 1110 based on at least the requestor location and requestor identifier, if such information is accessible from the mobile device. The healthcare prediction server 310 determines 1130 whether the emergency room services request is associated with an avoidable visit. If it is, the healthcare prediction server 310 routes or transmits a request 1142 to an alternative services provider and schedules 1150 a request. If the healthcare prediction server 310 determines 1130 that the emergency room services request is not associated with an avoidable visit, the healthcare prediction server 310 routes or transmits a request 1144 to an emergency room services provider.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A healthcare prediction system for providing prediction based healthcare recommendations, comprising:
    a first data warehouse system comprising a warehouse processor and a warehouse memory, the first data warehouse system further including a plurality of historical claims data;
    a healthcare prediction server in communication with the first data warehouse system, the healthcare prediction server comprising a processor and a memory, wherein the processor is configured to:
        receive an emergency room services request from a client device associated with a patient, the emergency room services request including a requestor location, a requestor identifier, and requestor symptoms;
        receive a first portion of the plurality of historical claims data from the data warehouse system, wherein the first portion includes associated historical outcome data;
        apply a geospatial prevalence engine to the first portion of the plurality of historical claims data and the requestor location to identify at least one locally prevalent disease having associated locally prevalent disease symptoms;
        apply a claims processing engine to the first portion of the plurality of historical claims data and the requestor identifier to predict whether the patient is associated with at least one prior avoidable emergency room claim, the claims processing engine comprising a prediction model that uses machine learning and is trained to predict that a given emergency room services request in the historical claims data is associated with an avoidable emergency room visit based on the historical outcome data associated with the historical claims data, the prediction model being generated by analyzing the historical claims data and the historical outcome data to identify one or more features that determine whether the emergency room visit is avoidable;
        upon determining at least one of a) that the patient is associated with at least one prior avoidable emergency room claim or b) that the requestor symptoms match the locally prevalent disease symptom, predict that the emergency room services request is associated with an avoidable emergency room visit based on the prediction of the claims processing engine; and
        transmit, to the client device associated with the patient, an alternative services request defined based on the requestor location, the requestor identifier, and the at least one symptom.

2. The healthcare prediction system of claim 1, wherein said processor is configured to:
    identify at least one alternative services provider by identifying potential providers within a defined geographic vicinity of the requestor location;
    identify at least one appointment window from the at least one alternative services provider; and
    transmit the alternative services request defined based on the requestor location, the requestor identifier, the at least one symptom, and the at least one alternative services provider.

3. The healthcare prediction system of claim 1, wherein said processor is configured to:
    create a predictive analytics model configured to provide a likelihood score that an emergency room services request is associated with an avoidable visit by processing the first portion of the plurality of historical claims data and the associated historical outcome data;

apply the predictive analytics model to the emergency room services request to obtain the likelihood score that the emergency room services request is associated with an avoidable visit; and upon determining that the likelihood score exceeds a first predetermined threshold indicating that the emergency room services request is associated with an avoidable visit, transmit the alternative services request defined based on the requestor location, the requestor identifier, and the at least one symptom.

4. The healthcare prediction system of claim 3, wherein said processor is configured to:

upon determining that the likelihood score exceeds a second predetermined threshold indicating that the emergency room services request is likely associated with an avoidable visit, transmit at least one supplemental question to the patient;

receive a supplemental emergency room services request in response to the at least one supplemental question;

apply the predictive analytics model to the supplemental emergency room services request to obtain the likelihood score that the emergency room services request is associated with an avoidable visit; and upon determining that the likelihood score exceeds the first predetermined threshold indicating that the emergency room services request is associated with an avoidable visit, transmit the alternative services request defined based on the requestor location, the requestor identifier, and the at least one symptom.

5. The healthcare prediction system of claim 1, wherein said processor is configured to:

receive a second portion of a plurality of electronic medical records and a third portion of electronic health records, wherein the second and third portions include associated historical outcome data from the data warehouse system;

apply a health record engine to the second portion of a plurality of electronic medical records and the third portion of electronic health records to create the prediction model configured to determine whether the emergency room services request is associated with an avoidable visit;

apply the prediction model to the emergency room services request to determine whether the emergency room services request is associated with an avoidable visit; and upon determining that the emergency room services request is associated with an avoidable visit, transmit the alternative services request defined based on the requestor location, the requestor identifier, and the at least one symptom.

6. The healthcare prediction system of claim 5, wherein said processor is configured to:

refine the predictive model based on location data associated with the second portion of a plurality of electronic medical records and the third portion of electronic health records to create a location based predictive model.

7. The healthcare prediction system of claim 5, wherein said processor is configured to:

process the second portion of a plurality of electronic medical records and the third portion of electronic health records into associated descriptive and diagnostic records; and apply the health record engine to the descriptive and diagnostic records to create the prediction model configured to determine whether the emergency room services request is associated with an avoidable visit.

8. A method for providing prediction based healthcare recommendations performed by a healthcare prediction server in communication with a first data warehouse system, the healthcare prediction server including a processor and a memory, the first data warehouse system including a warehouse processor and a warehouse memory, the first data warehouse system further including a plurality of historical claims data, said method comprising:

receiving an emergency room services request from a client device associated with a patient, the emergency room services request including a requestor location, a requestor identifier, and requestor symptoms;

receiving a first portion of the plurality of historical claims data from the data warehouse system, wherein the first portion includes associated historical outcome data;

applying a geospatial prevalence engine to the first portion of the plurality of historical claims data and the requestor location to identify at least one locally prevalent disease having associated locally prevalent disease symptoms;

applying a claims processing engine to the first portion of the plurality of historical claims data and the requestor identifier to predict whether the patient is associated with at least one prior avoidable emergency room claim, the claims processing engine comprising a prediction model that uses machine learning and is trained to predict that a given emergency room services request in the historical claims data is associated with an avoidable emergency room visit based on the historical outcome data associated with the historical claims data, the prediction model being generated by analyzing the historical claims data and the historical outcome data to identify one or more features that determine whether the emergency room visit is avoidable;

upon determining at least one of a) that the patient is associated with at least one prior avoidable emergency room claim or b) that the requestor symptoms match the locally prevalent disease symptom, predicting that the emergency room services request is associated with an avoidable emergency room visit based on the prediction of the claims processing engine; and transmitting, to the client device associated with the patient, an alternative services request defined based on the requestor location, the requestor identifier, and the at least one symptom.

9. The method of claim 8, further comprising:

identifying at least one alternative services provider by identifying potential providers within a defined geographic vicinity of the requestor location;

identifying at least one appointment window from the at least one alternative services provider; and transmitting the alternative services request defined based on the requestor location, the requestor identifier, the at least one symptom, and the at least one alternative services provider.

10. The method of claim 8, further comprising:

creating a predictive analytics model configured to provide a likelihood score that an emergency room services request is associated with an avoidable visit by processing the first portion of the plurality of historical claims data and the associated historical outcome data;

applying the predictive analytics model to the emergency room services request to obtain the likelihood score that the emergency room services request is associated with an avoidable visit; and upon determining that the likelihood score exceeds a first predetermined threshold indicating that the emergency room services request is associated with an avoidable visit, transmitting the alternative services request defined based on the requestor location, the requestor identifier, and the at least one symptom.

11. The method of claim 10, further comprising:

upon determining that the likelihood score exceeds a second predetermined threshold indicating that the emergency room services request is likely associated with an avoidable visit, transmitting at least one supplemental question to the patient;

receiving a supplemental emergency room services request in response to the at least one supplemental question;

applying the predictive analytics model to the supplemental emergency room services request to obtain the likelihood score that the emergency room services request is associated with an avoidable visit; and upon determining that the likelihood score exceeds the first predetermined threshold indicating that the emergency room services request is associated with an avoidable visit, transmitting the alternative services request defined based on the requestor location, the requestor identifier, and the at least one symptom.

12. The method of claim 8, further comprising:

receiving a second portion of a plurality of electronic medical records and a third portion of electronic health records, wherein the second and third portions include associated historical outcome data from the data warehouse system;

applying a health record engine to the second portion of a plurality of electronic medical records and the third portion of electronic health records to create the prediction model configured to determine whether the emergency room services request is associated with an avoidable visit;

applying the prediction model to the emergency room services request to determine whether the emergency room services request is associated with an avoidable visit; and upon determining that the emergency room services request is associated with an avoidable visit, transmitting the alternative services request defined based on the requestor location, the requestor identifier, and the at least one symptom.

13. The method of claim 12, further comprising:

refining the predictive model based on location data associated with the second portion of a plurality of electronic medical records and the third portion of electronic health records to create a location based predictive model.

14. The method of claim 12, further comprising:

processing the second portion of a plurality of electronic medical records and the third portion of electronic health records into associated descriptive and diagnostic records; and applying the health record engine to the descriptive and diagnostic records to create the prediction model configured to determine whether the emergency room services request is associated with an avoidable visit.

15. A healthcare prediction server for providing prediction based healthcare recommendations in communication with a first data warehouse system, the healthcare prediction server comprising a processor and a memory, the first data warehouse system including a warehouse processor and a warehouse memory, the first data warehouse system further including a plurality of historical claims data, wherein the processor is configured to:

receive an emergency room services request from a client device associated with a patient, the emergency room services request including a requestor location, a requestor identifier, and requestor symptoms;

receive a first portion of the plurality of historical claims data from the data warehouse system, wherein the first portion includes associated historical outcome data;

apply a geospatial prevalence engine to the first portion of the plurality of historical claims data and the requestor location to identify at least one locally prevalent disease having associated locally prevalent disease symptoms;

apply a claims processing engine to the first portion of the plurality of historical claims data and the requestor identifier to predict whether the patient is associated with at least one prior avoidable emergency room claim, the claims processing engine comprising a prediction model that uses machine learning and is trained to predict that a given emergency room services request in the historical claims data is associated with an avoidable emergency room visit based on the historical outcome data associated with the historical claims data, the prediction model being generated by analyzing the historical claims data and the historical outcome data to identify one or more features that determine whether the emergency room visit is avoidable;

upon determining at least one of a) that the patient is associated with at least one prior avoidable emergency room claim or b) that the requestor symptoms match the locally prevalent disease symptom, predict that the emergency room services request is associated with an avoidable emergency room visit based on the prediction of the claims processing engine; and transmit, to the client device associated with the patient, an alternative services request defined based on the requestor location, the requestor identifier, and the at least one symptom.

16. The healthcare prediction server of claim 15, further configured to:

identify at least one alternative services provider by identifying potential providers within a defined geographic vicinity of the requestor location;

identify at least one appointment window from the at least one alternative services provider; and transmit the alternative services request defined based on the requestor location, the requestor identifier, the at least one symptom, and the at least one alternative services provider.

17. The healthcare prediction server of claim 15, further configured to:

create a predictive analytics model configured to provide a likelihood score that an emergency room services request is associated with an avoidable visit by processing the first portion of the plurality of historical claims data and the associated historical outcome data;

apply the predictive analytics model to the emergency room services request to obtain the likelihood score that the emergency room services request is associated with an avoidable visit; and upon determining that the likelihood score exceeds a first predetermined threshold indicating that the emergency room services request is associated with an avoidable visit, transmit the alternative services request defined based on the requestor location, the requestor identifier, and the at least one symptom.

18. The healthcare prediction server of claim 17, further configured to:
   upon determining that the likelihood score exceeds a second predetermined threshold indicating that the emergency room services request is likely associated with an avoidable visit, transmit at least one supplemental question to the patient;
   receive a supplemental emergency room services request in response to the at least one supplemental question;
   apply the predictive analytics model to the supplemental emergency room services request to obtain the likelihood score that the emergency room services request is associated with an avoidable visit; and
   upon determining that the likelihood score exceeds the first predetermined threshold indicating that the emergency room services request is associated with an avoidable visit, transmit the alternative services request defined based on the requestor location, the requestor identifier, and the at least one symptom.

19. The healthcare prediction server of claim 15, further configured to:
   receive a second portion of a plurality of electronic medical records and a third portion of electronic health records, wherein the second and third portions include associated historical outcome data from the data warehouse system;
   apply a health record engine to the second portion of a plurality of electronic medical records and the third portion of electronic health records to create the prediction model configured to determine whether the emergency room services request is associated with an avoidable visit;
   apply the prediction model to the emergency room services request to determine whether the emergency room services request is associated with an avoidable visit; and
   upon determining that the emergency room services request is associated with an avoidable visit, transmit the alternative services request defined based on the requestor location, the requestor identifier, and the at least one symptom.

20. The healthcare prediction server of claim 19, wherein said processor is configured to:
   refine the prediction model based on location data associated with the second portion of a plurality of electronic medical records and the third portion of electronic health records to create a location based predictive model.

* * * * *